United States Patent [19]

Rosenfeld et al.

[11] Patent Number: 5,254,785
[45] Date of Patent: Oct. 19, 1993

[54] PRODUCTION OF OLEFINS

[75] Inventors: David D. Rosenfeld; Derrick D. Pete, both of Houston; Larry L. Iaccino, Friendswood; Barrington M. Hammond, Houston, all of Tex.

[73] Assignee: Exxon Chemical Patents Inc., Linden, N.J.

[21] Appl. No.: 895,958

[22] Filed: Jun. 9, 1992

[51] Int. Cl.$^5$ ............................................. C07C 1/00
[52] U.S. Cl. ................................... 585/640; 585/639; 585/638
[58] Field of Search .................... 585/638, 639, 640

[56] References Cited

U.S. PATENT DOCUMENTS

| | | | |
|---|---|---|---|
| 3,240,697 | 3/1966 | Miale | 585/640 |
| 4,467,133 | 8/1984 | Chang et al. | 585/733 |
| 4,544,793 | 10/1985 | Okada et al. | 585/640 |
| 4,691,073 | 9/1987 | Michaelson | 585/640 |

Primary Examiner—Patrick P. Garvin
Assistant Examiner—E. D. Irzinski
Attorney, Agent, or Firm—Linda K. Russell

[57] ABSTRACT

The present invention provides a process for cracking or decomposing a feedstream containing a major proportion of at least one dialkyl ether to produce the corresponding olefins comprising contacting the feedstream with a faujasite aluminosilicate catalyst which is characterized in that at least about 50 wt. % of the alkali metal content originally present in said faujasite has been exchanged by at least one alkaline earth metal. The decomposition is preferably conducted in the vapor phase at preferred temperatures in the range of from about 125° F. to about 600° F. The process offers the advantages of longer catalyst life coupled with high yield and selectivity rates towards olefin production.

21 Claims, No Drawings

PRODUCTION OF OLEFINS

BACKGROUND OF THE INVENTION

1. Field of the Invention

The present invention relates to a method for the production of tertiary olefins. More particularly, it relates to a method for the production of pure tertiary olefins by the decomposition of alkyl tert-alkyl ethers in the presence of a new and improved catalyst based on an alkaline earth exchanged faujasite.

2. Description of Related Art

Olefins, particularly tertiary olefins, may be commercially produced by the sulfuric acid extraction of such olefins from mixtures containing them obtained e.g., by steam cracking of petroleum feeds. Since this method uses sulfuric acid of high concentration, the use of expensive materials in the fabrication of the extraction apparatus is essential. Also, dilution of the acid to promote olefin recovery and reconcentrating the acid prior to recycling are required and are expensive. In addition, this method is not always advantageous industrially because tertiary olefins are subject to side reactions such as polymerization, hydration and the like during extraction with concentrated sulfuric acid.

It is also known that tertiary olefins may be prepared by reacting them selectively from such feeds with a primary alcohol in the presence of a acid catalyst to produce the corresponding alkyl tert-alkyl ethers. The tert-alkyl ethers are primarily formed, since the secondary olefins react very slowly and the primary olefins are completely inert. Such alkyl tert-alkyl ethers may then be easily separated and subsequently decomposed back to the tertiary olefins and the primary alcohol.

For producing tertiary olefins from alkyl tert-alkyl ethers, there have been proposed methods using various catalysts: For example aluminum compounds supported on silica or other carriers (U.S. Pat. No. 4,398,051); phosphoric acid on various supports (U.S. Pat. No. 4,320,232); and metal containing weakly acidic components on a carrier of >20 $M^2$/gm surface area (British Pat. No. 1,173,128). In addition, inferior results are disclosed as being obtained utilizing carriers alone in the decomposition of methyl tertiary butyl ether (U.S. Pat. No. 4,398,051) and utilizing $H_2SO_4$ treated clay in the decomposition of t-alkyl ether alkanols (U.S. Pat. No. 4,254,290).

One of the main disadvantages of such processes is that the disclosed catalysts do not have good catalyst life in that higher and higher temperatures, which eventually become limiting, are required to maintain high conversion of the alkyl tert-alkyl ethers. Additionally, larger amounts of the dialkyl ether by-product are produced as the catalyst ages with the disadvantage of a reduction in yield of the desired tertiary olefin. This lack of good catalyst life may be due to the instability of the catalyst, to high temperatures being required for good conversion thus promoting fouling, to the catalyst itself promoting fouling or to any or all of these. Also, a number of the catalysts such as ion exchange resins cannot be regenerated after use.

More recently, processes have been discovered which provide improved yields of tertiary olefin product. For example, U.S. Pat. No. 4,691,073 discloses a process for preparing tertiary olefins from alkyl tertiary alkyl ethers comprising contacting the ether with a catalyst which has been prepared by reacting a clay with HF and/or HCl and calcining the resultant clay product. Although the process produces very high yields and selectivity towards the production of tertiary olefin products, these catalysts often tend to become deactivated as a consequence of coke and/or polymeric build up in a relatively short on-stream time. Also, the aluminosilicate structure of many clays is not sufficiently stable to withstand repeated high temperature regenerations required to remove catalyst deposits.

Natural and synthetic faujasite catalysts are known for use in the conversion or pyrolysis of ethers and alcohols into olefins or distillate range hydrocarbons. For example, U.S. Pat. No. 4,467,133 discloses the conversion of methanol into a distillate range hydrocarbon mixture by passing methanol over a rare earth exchanged faujasite (such as zeolite X or Y) at a temperature below 6000° F. U.S. Pat. No. 4,544,793 discloses a similar process using an exchanged aluminosilicate catalyst which has a specific X-ray diffraction pattern as shown in Table 1 of the patent.

SUMMARY OF THE INVENTION

The present invention provides a process for cracking or decomposing a feedstream containing a major proportion of at least one dialkyl ether having at least about 5 carbon atoms to produce the corresponding olefins, comprising contacting the feedstream with a faujasite aluminosilicate catalyst which is characterized in that at least about 50 wt. % of the alkali metal content originally present in said faujasite has been exchanged by at least one alkaline earth metal. The decomposition is preferably conducted in the vapor phase at preferred temperatures in the range of from about 125° F. to about 600° F. The process offers the advantages of longer catalyst life coupled with high yield and selectivity rates towards olefin production, as well as rates of conversion of ether to olefin in excess of about 60% by weight, preferably in excess of about 90% by weight.

DETAILED DESCRIPTION OF THE INVENTION

The catalyst which may be used in the process of this invention is based on a synthetic faujasite referred to as zeolite Y. This is a crystalline aluminosilicate well known in the art and is disclosed in U.S. Pat. No. 3,130,007, the complete disclosure of which is incorporated herein by reference. The preferred faujasite has a silica to alumina ratio in the range of from about 3 to 1 to about 6 to 1 and pore dimensions greater than about 6 angstroms.

This zeolite material may be activated for the ether decomposition reaction by base exchanging the alkali metal originally present in said zeolite, e.g. sodium, with one or a mixture of alkaline earth metals such that at least 50% by weight of the alkali metal is replaced by the alkaline earth metal. It is preferred to conduct the exchange such that as many as possible of the original alkali metal ions are so exchanged, e.g., at least about 75% by weight and more preferably at least about 85% by weight. Most preferably the exchange is such that the original alkali metal content of the zeolite is reduced to a level below about 1% by weight and the degree of exchange is about 90% or above. Suitable alkaline earth exchange metals are calcium, barium and strontium, with calcium being most preferred.

Base exchange may be conducted by contacting the zeolite (which has been preferably previously calcined) one or more times with an aqueous solution containing an alkaline earth metal salt dissolved therein at a temperature ranging from ambient up to about 185° F. A wide variety of salts may be employed such as the chlorides, bromides, carbonates, sulfates, nitrates and the like so long as such salts are soluble in water such that ion transfer can take place. Calcium chloride is the preferred salt. The concentration of the salt in solution may range from about 0.1 to about 25% by weight and should be sufficient to provide a slight excess of the stoichiometric amount of exchange cation.

After an exchange contact period which may range from about 60 minutes to about 24 hours, the exchanged zeolite is separated from the exchange solution, washed and dried. The exchange can be repeated one or more times if necessary in order to replace the maximum number of alkali metal ions with alkaline earth metal ions.

Other exchange processes may also be employed, such as the so called incipient wetness method, wherein the zeolite is infused with exchange solution to form a paste which is then dried.

The catalyst may be used in the process without additional binder or it may be formulated with a binder or carrier material such as alumina, silica, clay or an alumina/silica mixture. Bound catalyst may be prepared by mixing the powdered catalyst with water and from about 5 to about 40% by weight binder to form a paste, and extruding and drying the paste to form small pellets. The bound catalyst is then preferably further activated by calcination at 650° F.–1100° F. for a period of about 10 minutes up to a period of hours, e.g., 24 hours. The ion exchange process may be conducted prior to or subsequent to the formulation of such bound zeolites, preferably subsequent to such formulation.

Ethers which may be cracked using the catalyst of this invention generally contain from about 5 to about 12 carbon atoms, more preferably from about 5 to 9 carbon atoms and most preferably from about 5 to 8 carbon atoms. Preferred ethers include tertiary alkyl ethers such as tertiary butyl methyl ether and tertiary butyl ethyl ether, and tertiary amyl counterparts including the methyl and ethyl ethers. Typical feedstreams for the process generally contain at least about 70% up to 100% by weight of the tertiary alkyl ether, with the balance of the feedstream comprising primarily a mixture of saturated and unsaturated hydrocarbons and alcohols such as methanol or tertiary alkylalcohols.

The decomposition reaction is conducted in any suitable reactor which is packed with one or more beds of the alkaline earth exchanged catalyst. Reactor operating temperatures for this process are generally relatively low, ranging from about 125 0 to 600° F. and more preferably from about 240° F. to about 500° F. and most preferably from about 280° F. to 380° F. Operating pressure may range from atmospheric to about 250 psig, with 50 to 125 psig being preferred. Pressure should be such that the reaction occurs substantially in the vapor phase. The reactor should also be equipped with a suitable temperature controlling means such that the desired operating temperatures can be maintained or adjusted in the reactor.

The reaction is carried out at a spatial velocity expressed in terms of weight of organic feed per unit weight of catalyst per hour in the range of from about 0.5 to 100 WHSV, preferably from about 1 to about 20 WHSV.

The process is especially suited for the conversion of fractions containing tertiary amylmethyl ether into corresponding isopentene olefins such as 2-methyl-2-butene or 2-methyl-1-butene, as well as conversion of fractions containing methyl tertiary butyl ether into isobutylene. A particular advantage of the process is that the decomposition product contains a very low content of the corresponding alkanes such as isobutane or isopentane which are very difficult to separate from their olefin counterparts.

The following examples are illustrative of the invention.

EXAMPLE 1

A calcium exchanged zeolite Y catalyst was prepared as follows: 108.3 grams of pellets of zeolite Y (LZY-52, available from UOP) which contained 20% by weight of alumina as a binder were packed into an 18 inch glass column. The column was then flushed with 100 ml of ultra high pure water (pH-6.7) at a temperature of 150° F.

A solution of 217 g of calcium chloride in 3500 ml of ultra high pure water was formed and this solution was then passed through the packed zeolite bed at a rate of 2 ml per minute at 150° F. The packed zeolite was then washed with additional pure water until the effluent was essentially free of chloride ions as indicated by a negative silver nitrate test. The exchanged zeolite was then dried overnight under a vacuum at ambient temperatures and then dried at 212° F. for 8 hours under vacuum. Analysis showed that about 90% by weight of the original sodium ions present in the zeolite had been exchanged by calcium ions.

EXAMPLE 2

The exchanged zeolite of Example 1 was crushed and sieved to 20–40 mesh and packed into a 12 inch by 0.25 inch stainless steel reactor column which was then connected to a feed line. The reactor was placed in a circulating hot air oven and also connected to an effluent collector line.

A feed stream containing 95+% of tertiary butyl methyl ether was preheated and passed into the inlet of the reactor at a constant temperature maintained at about 355° F., at a pressure of 90 psig and at a WHSV in the range of from about 3 to 5. Reaction product removed from the discharge of the reactor showed an initial conversion rate of greater than 95% of tertiary butyl methyl ether to isobutylene. The process was continued under constant conditions of pressure and temperature until the % conversion to isobutylene dropped below 90%. The elapsed time to below 90% conversion was measured at 676 hours.

EXAMPLE 3

Example 2 was repeated under the conditions set forth except the catalyst employed was a hydrogen fluoride treated and calcined attapulgite clay as disclosed in U.S. Pat. No. 4,691,073. The on stream time for isobutylene conversion to drop below 90% was measured as 46 hours.

A comparison of the results in Examples 2 and 3 demonstrates that the catalyst of this invention provides high yields of olefin over a longer period of time than the HF attapulgite of the prior art, i.e., 676 hours vs. only 46 hours.

EXAMPLE 4

In this example, a number of prior art catalysts were evaluated in the pilot plant for their resistance to catalyst deactivation in the ether decomposition process. In this test, the initial temperature in the reactor was set at 340° F. and the temperature was gradually raised to 380° F. as needed to maintain 90% conversion of the tertiary butyl methyl ether to isobutylene. The hours on stream before conversion at the peak temperature of 380° F. dropped below 90% were recorded in each case. Some tests were terminated sooner if unacceptable high levels of undesirable by-products were formed. The flow was maintained at about 3.6 WHSV and 90 psig pressure. Results are shown in Table 1.

TABLE 1

| Catalyst | Hours on Feed |
| --- | --- |
| HF Attapulgite | 400 |
| Ca—Y | 1100** |
| Ca—X | 300 |
| ZSM-5 | 576* |
| Ultra stable-Y | 164* |
| Beta Zeolite (Powder) | 120* |
| Mg—Y | 96 |
| Na—Y | 72* |
| Mordenite | 48 |
| Erionite (Powder) | 24 |
| Na—X | 48 |
| Silicalite | 24 |
| Rare earth Y | 72 |
| H—Y (acid form) | 300* |

*Test was terminated due to formation of high levels of by-product.
**Test was terminated before the maximum temperature was reached. Ether conversion was still at 90%

This data clearly demonstrates the superiority of the catalyst of this invention (CaY) when compared with HF Attapulgite and other catalysts of the prior art. CaY had the lowest average rate of deactivation of about 0.36° F. per day.

What it is claimed:

1. A process for the selective conversion of alkyl ethers containing about 5 to 12 carbon atoms to their corresponding olefins comprising contacting a feed containing one or a mixture of said ethers with a faujasite catalyst having a silica to alumina ratio of from about 3 to 1 to about 6 to 1 and a pore dimension in excess of about 6 angstroms, under conditions of temperature and pressure sufficient to convert a substantial quantity of ether to olefin, said catalyst further characterized that at least 50% by weight of the original content of alkali metal present in said catalyst has been exchanged with at least one alkaline earth metal.

2. The process of claim 1 wherein said catalyst is zeolite Y.

3. The process of claim 2 wherein said temperature ranges from about 125° F. to about 600° F.

4. The process of claim 2 wherein said pressure ranges from about atmospheric to about 250 psig.

5. The process of claim 2 wherein the flow rate of feed past said catalyst is in the range of from about 0.5 to 100 WHSV.

6. The process of claim 2 wherein at least about 85% by weight of said alkali metal ions are exchanged.

7. The process of claim 2 wherein said catalyst further contains from about 5 to about 40% by weight of a binder selected from the group consisting of alumina, silica, clay or alumina/silica mixture.

8. The process of claim 2 wherein said alkaline earth metal is calcium.

9. The process of claim 2 wherein said ether is a tertiary alkyl ether containing from about 5 to about 8 carbon atoms.

10. The process of claim 9 wherein said ether comprises tertiary butyl methyl ether.

11. The process of claim 9 wherein said ether comprises tertiary amyl methyl ether.

12. The process of claim 2 wherein the rate of conversion of ether to olefin is at least 60% by weight.

13. A process for the selective conversion of tertiary butyl methyl ether or tertiary amyl methyl ether into isobutylene or isopentenes respectively comprising contacting a feed containing at least one of said ethers with zeolite Y catalyst, at least about 50% by weight of the original sodium metal content of which has been exchanged with calcium, at a temperature in the range of about 240° F. to 500° F. and pressures within the range of about 50–125 psig, and recovering said olefin product.

14. The process of claim 13 wherein at least about 90% by weight of said sodium metal has been exchanged.

15. The process of claim 13 wherein said temperature is in the range of about 280° F. to 380° F.

16. The process of claim 13 wherein said feed is passed through said catalyst at a rate of from about 1 to about 20 WHSV.

17. The process of claim 13 wherein at least 90% of said ether is converted to said olefin.

18. The process of claim 13 wherein said ether comprises tertiary butyl methyl ether.

19. The process of claim 13 wherein said ether comprises tertiary amyl methyl ether.

20. The process of claim 13 wherein said zeolite Y further contains from about 5 to about 40% by weight of a binder selected from the group consisting of alumina, silica, clay or alumina/silica mixture.

21. The process of claim 13 wherein said zeolite Y has been calcined by heating to a temperature in the range of from about 650° F. to 1100° F. prior to said exchange.

* * * * *